United States Patent
Barbour et al.

(10) Patent No.: US 6,795,195 B1
(45) Date of Patent: Sep. 21, 2004

(54) SYSTEM AND METHOD FOR TOMOGRAPHIC IMAGING OF DYNAMIC PROPERTIES OF A SCATTERING MEDIUM

(75) Inventors: Randall L. Barbour, Glen Head, NY (US); Christoph H. Schmitz, Brooklyn, NY (US)

(73) Assignee: Research Foundation of State University of New York, Albany, NY (US)

( * ) Notice: Subject to any disclaimer, the term of this patent is extended or adjusted under 35 U.S.C. 154(b) by 0 days.

(21) Appl. No.: 10/088,254

(22) PCT Filed: Sep. 14, 2000

(86) PCT No.: PCT/US00/25155
§ 371 (c)(1),
(2), (4) Date: Aug. 29, 2002

(87) PCT Pub. No.: WO01/20306
PCT Pub. Date: Mar. 22, 2001

Related U.S. Application Data
(60) Provisional application No. 60/154,099, filed on Sep. 15, 1999, and provisional application No. 60/153,926, filed on Sep. 14, 1999.

(51) Int. Cl.[7] ............................................. G01N 21/47
(52) U.S. Cl. ..................................................... 356/446
(58) Field of Search ................................ 356/445–448, 356/39; 250/341, 212.1, 339, 343, 346, 252.1; 382/128, 131

(56) References Cited

U.S. PATENT DOCUMENTS

| | | | | |
|---|---|---|---|---|
| 4,810,875 A | * | 3/1989 | Wyatt ..................... | 250/227.11 |
| 5,137,355 A | * | 8/1992 | Barbour et al. .............. | 356/342 |
| 5,351,677 A | * | 10/1994 | Kami et al. ................. | 600/109 |
| 5,353,799 A | * | 10/1994 | Chance ........................ | 600/473 |
| 5,365,066 A | * | 11/1994 | Krueger et al. ........... | 250/341.2 |
| 5,386,819 A | * | 2/1995 | Kaneko et al. ............. | 600/177 |
| 5,625,458 A | * | 4/1997 | Alfano et al. ............... | 356/446 |
| 5,676,141 A | * | 10/1997 | Hollub ....................... | 600/323 |
| 5,865,754 A | * | 2/1999 | Sevick-Muraca et al. ... | 600/476 |
| 5,994,690 A | | 11/1999 | Kulkarni et al. | |
| 6,081,322 A | * | 6/2000 | Barbour ..................... | 356/73.1 |
| 6,377,842 B1 | * | 4/2002 | Pogue et al. ................ | 600/478 |
| 6,485,413 B1 | * | 11/2002 | Boppart et al. ............. | 600/160 |
| 6,590,651 B1 | * | 7/2003 | Bambot et al. ............. | 356/338 |
| 6,608,717 B1 | * | 8/2003 | Medford et al. ............ | 359/368 |

* cited by examiner

Primary Examiner—Michael P. Stafira
(74) Attorney, Agent, or Firm—Scully, Scott, Murphy & Presser

(57) ABSTRACT

A system and method for the detection and three dimensional imaging of absorption and scattering properties of a medium such as human tissue is described. According to one embodiment of the invention, the system directs optical energy toward a turbid medium from at least one source and detects optical energy emerging from the turbid medium at a plurality of locations using at least one detector. The optical energy emerging from the medium and entering the detector originates from the source is scattered by the medium. The system then generates an image representing interior structure of the turbid medium based on the detected optical energy emerging from the medium. Generating the image includes a time-series analysis.

51 Claims, 15 Drawing Sheets

Cont'd to FIG. 12B

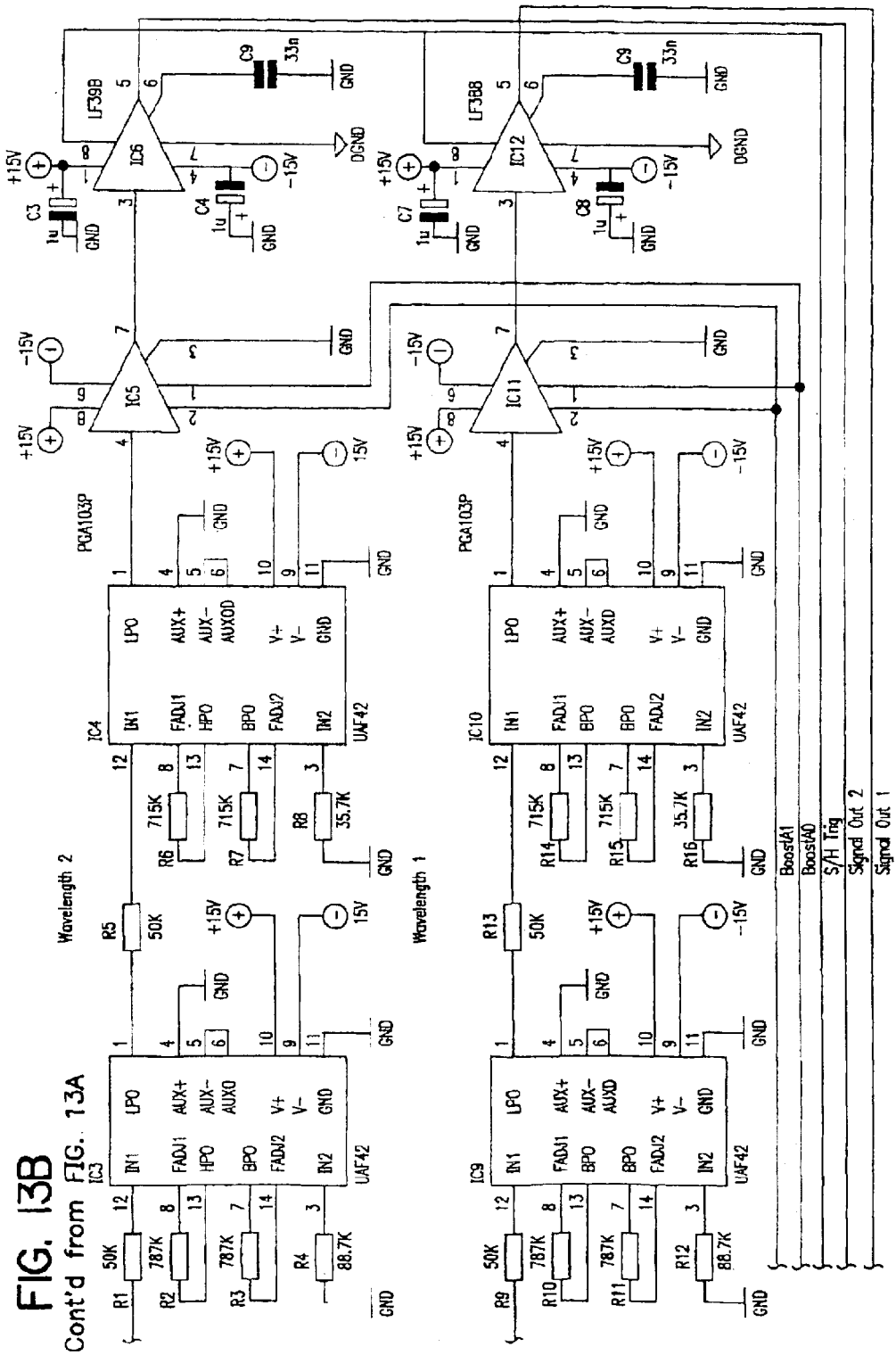
FIG. 13B Cont'd from FIG. 13A

SYSTEM AND METHOD FOR TOMOGRAPHIC IMAGING OF DYNAMIC PROPERTIES OF A SCATTERING MEDIUM

This application claims the benefit under 35 U.S.C. § 120 of prior U.S. Provisional Patent Application Serial Nos. 60/153,926 filed Sep. 14, 1999, entitled DYNAMIC TOMOGRAPHY IN A SCATTERING MEDIUM and 60/154,099 filed Sep. 15, 1999, entitled DYNAMIC TOMOGRAPHY IN A SCATTERING MEDIUM.

This application is related to copending application Ser. No. PCT/US00/25136 filed on the same date as this application, entitled "METHOD AND SYSTEM FOR IMAGING THE DYNAMICS OF SCATTERING MEDIUM" by inventor R. Barbour is hereby incorporated by reference (hereinafter the "Barbour 4147PC2 application"). The counterpart U.S. patent application is app. Ser. No. 10/088,190, filed Mar. 14, 2002.

This application is related to copending application Ser. No. PCT/US00/25157 filed on the same date as this application, entitled "METHOD AND SYSTEM FOR ENHANCED IMAGING OF A SCATTERING MEDIUM" by inventors R. Barbour and Y. Pei and is hereby incorporated by reference (hereinafter the "Barbour 4149PC1 application"). The counterpart U.S. patent application is app. Ser. No. 10/088,185, filed Mar. 14, 2002.

This application is also related to copending application Ser. No. PCT/US00/2515, filed on the same date as this application, entitled "IMAGING OF SCATTERING MEDIA USING RELATIVE DETECTOR VALUES" by inventor R. Barbour and is hereby incorporated by reference (hereinafter the "Barbour 4149PC2 application"). The counterpart U.S. patent application is app. Ser. No. 10/088,192, filed Mar. 14 2002.

This invention was made with U.S. Government support under contract number CA-RO166184-02A, awarded by the National Cancer institute. The U.S. Government has certain rights in the invention.

FIELD OF THE INVENTION

The invention relates to a system and method for tomographic imaging of dynamic properties of a scattering medium, which may have special application to medical imaging, and in particular to systems and methods for tomographic imaging using near infrared energy to image time variations in the optical properties of tissue.

BACKGROUND OF THE INVENTION

Contrary to imaging methods relying on the use of ionizing radiation and/or toxic/radioactive contrast agents, near infra-red (NIR)-imaging methods bear no known risk of causing harm to the patient. The dose of optical intensity used remains far below the threshold of thermal damage and is therefore safe. In the regime of wavelength/intensity/power used, there are no effects on patient tissue that accumulate with increasing NIR dose due to over-all irradiation time.

The general technology involved in optical tomography is developed and understood, so that, compared to other cross-sectional imaging techniques such as MRI, X-ray CT, and the like, only moderate costs and relatively small-sized devices are required. Optical tomography especially gains from the development of small, economical, yet powerful semiconductor lasers (laser diodes) and the availability of highly integrated, economical off-the-shelf data processing electronics suitable for the application. Moreover, the availability of powerful yet inexpensive computers contributes to the attractiveness of optical tomography since a significant computational effort may be necessary for both image reconstruction and data analysis.

Optical tomography yields insights into anatomy and physiology that are unavailable from other imaging methods, since the underlying biochemical activities of physiological processes almost always leads to changes in tissue optical properties. For example, imaging blood content and oxygenation is of interest. Blood shows prominent absorption spectra in the NIR region and vascular dynamics and blood oxygenation play a major role in physiology/pathology.

However, cross-sectional or volumetric imaging of dynamic features in large tissue structures is not extractable with current optical imaging methods. At present, whereas a variety of methods involving imaging and non-imaging modalities are available for assessing specific features of the vasculature, none of these assess dynamic properties based on measures of hemoglobin states. For instance, detailed images of the vascular architecture involving larger vessels (>1 mm dia.) can be provided using x-ray enhanced contrast imaging or MR angiography. These methods however are insensitive to hemoglobin states and only indirectly provide measures of altered blood flow. The latter is well accomplished, in the case of larger vessels, using Doppler ultrasound, and for near-surface microvessels by laser Doppler measurements, but each is insensitive to variations in tissue blood volume or blood oxygenation. Ultrasound measurements are also limited by their ability to penetrate bone. Other methods are available, (e.g., pulse volume recording, magnetic resonance (MR) BOLD method, radioscintigraphic methods), and each is able to sample, either directly or indirectly, only a portion of the indicated desired measures.

Thus, there is a need for a system and method of data collection providing cross-sectional or volumetric imaging of dynamic features in large tissue structures

SUMMARY OF THE INVENTION

The present invention provides a system and method for generating an image of dynamic properties in a scattering medium. The system includes an energy source, such as a NIR emitting source, and a detection system to measure received energy. In an exemplary embodiment, the detection system has at least one photo-detector such as a photodiode, a means for rapid adjustment of signal gain, and a device for retaining a measured response in order to investigate the dynamic variations in the optical properties of tissues. Depending on the implementation, the detection system further may also include at least one means for separating a plurality of signals from the photo-receiver when multiple energy sources are used simultaneously. This simultaneous use of multiple energy sources allows the use of different wavelengths and/or different source locations at the same time.

In one implementation using optical tomographic imaging, a specimen is exposed to NIR light emitted from at least one laser diode. Furthermore an imaging head may be utilized that contains means for positioning at least one source location and / or at least one detector location with respect to the medium. The energy detector may use an energy collecting element, such as an optical fiber to transmit the received energy. The energy detector is responsive to the energy or light emerging from the specimen. In accordance with the invention, the signal from the detector is selectively enhanced in gain to increase the dynamic measurement range. The method may further include separating via at least one lock-in amplifier a plurality of signals generated by multiple energy sources. In addition, the method allows simultaneous measurements of signals produced by the NIR light by means of a sample-and-hold circuit when more than one detector fiber is used.

BRIEF DESCRIPTION OF THE FIGURES

For a better understanding of the invention, together with the various features and advantages thereof, reference should be made to the following detailed description of the preferred embodiments and to the accompanying drawings wherein.

DETAILED DESCRIPTION OF THE INVENTION

Figure 1:
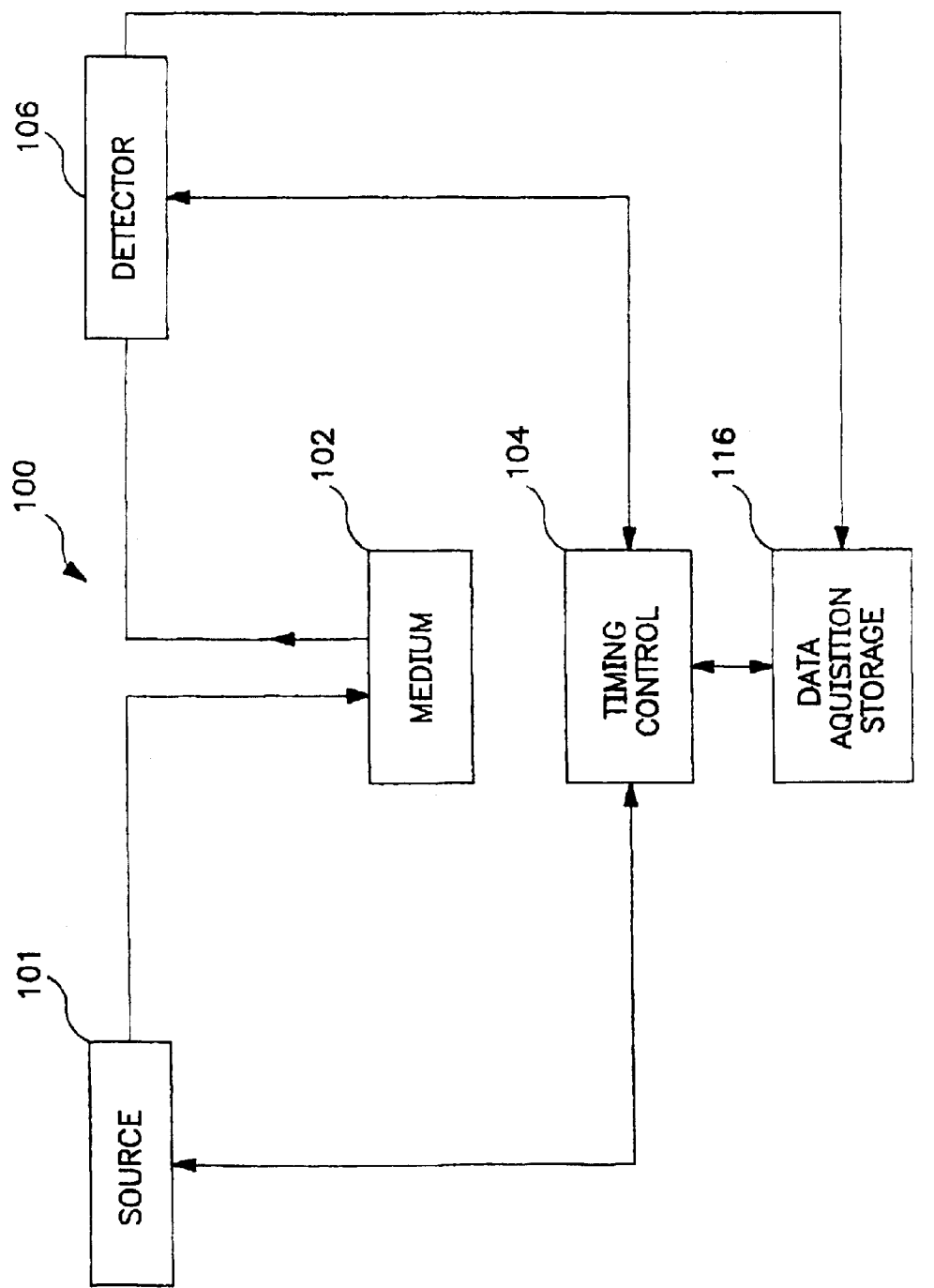
FIG. 1 is a block diagram of one embodiment of a system according to the invention.

The objective of the invention is to provide a system and method capable to extract dynamics in properties of a scattering medium. The use of the invention's system and method has several applications including, but not limited to, medical imaging applications. Although the methods described herein focus on tomographic imaging the dynamic properties of hemoglobin states and tissue using optical tomography, with an imaging source generating multiple wavelengths in the NIR region, it is appreciated that the invention is applicable to any medium that is able to scatter the propagating energy from any energy source, including external energy sources such as those sources located outside the medium and/or internal sources such as those energy sources located inside the medium. For example, other media includes, but are not limited to, medium from mammals, botanical life, aquatic life, or invertebrates; oceans or water masses; foggy or gaseous-atmospheres; earth strata; industrial materials; man-made or naturally occurring chemicals and the like. Energy sources include, but are not limited to, non-laser optical sources like LED and high-pressure incandescent lamps and lasers sources such as laser diodes, solid state lasers such as titanium-sapphire laser and ruby laser, dye laser and other electromagnetic sources, acoustic energy, acoustic energy produced by optical energy, optical energy, and any combinations thereof Similarly the means to detect the signal produced by the energy source is not limited to photodiode implementation discussed in one of the preferred embodiments further described herein. Other detectors can be used with the principles of the present invention for the purpose of tomographic imaging the dynamic properties of a medium. Such detectors include for example, but are not limited to, photodiodes, PIN diodes (PIN), Avalanche Photodiodes (APD), charge couple device (CCD), charge inductive device (CID), photo-multiplier tubes (PMT), multi-channel plate (MCP), acoustic transducers and the like.

The present invention builds upon previous disclosures in U.S. Pat. Nos. 5,137,355 ("the '355 patent") entitled "Method of Imaging a Random Medium" ("the '355 patent") and U.S. Pat. No. 6,081,322 ("the '322 patent") entitled "NIR Clinical Opti-Scan System", the disclosures of both the '355 and '322 patents are incorporated herein by reference. Disclosed in these patents is an approach to optical tomography, and the instrumentation required to accomplish the tomography. The modifications in the present invention provide fast data acquisition, and new imaging head designs. Fast data acquisition allows accurate sampling of dynamic features. The modification in the imaging head allows accommodation of different size targets (e.g., breast); the stabilization of the target against motion artifacts; conforming the target to a simple well-defined geometry; and knowledge of source and detector positioning on or about the target. All of the enumerated features listed above for the imaging head is crucial for accurate image reconstruction.

Additionally, the present invention uses detector circuitry that allows quick adaptation of the measurement range to the signal strength thereby increasing the over-all dynamic range. "Dynamic range" for the purposes of this description means the ratio between the highest and lowest detectable signal. This makes the circuitry suitable for use with source-detector distances that can vary significantly during the data collection, thereby allowing fast data acquisition over wide viewing angles. For instance, we are aware that dynamic features of dense scattering media may be extractable from measurements using a single source and single detector at a fixed distance between each other. Depending on the implementation, such an arrangement could be made using a detector of relatively small dynamic range. Although we are aware of the possible usefulness of such a measurement, our invention allows the measurement of dynamics in optical properties of dense scattering media using source-detector pairs over a wide range of distances (e.g., greater than or about 5 cm). Such fall tomographic measurements allow for improved accuracy in image reconstruction.

Depending upon the implementation, it is within the scope of the present invention to include those embodiments using a restricted source detector distance and therefore not requiring fast gain adjustment. For example, in one embodiment, the system of the present invention can also be operated using detector channels of low-dynamic range (e.g., 1:10.00) when detector fibers of a fixed distance from the source are being used for the measurement (e.g., the detector opposite the source).

The data collection scheme of the present invention disclosed herein provides time-series of raw data sets that provide useful information about dynamic properties of the scattering medium without any further image reconstruction. For example, by displaying the raw data in a color mapping format, features can be extracted by sole visual inspection. In addition to that, analysis algorithms of various types such as, but not limited to, linear and non-linear time-series analysis or pattern recognition methods can be applied to the series of raw data. The advantage of using these analytical methods is the improved capability to reveal dynamic signatures in the signals.

In another implementation, image reconstruction methods may be applied to the sets of raw data thereby providing time series of cross-sectional images of the scattering medium. For these implementations, analysis methods of various types such as, but not limited to, linear and non-linear time-series analysis, filtering, or pattern recognition methods can be applied. The advantage of using such analysis is the improved extraction of dynamic features and cross-sectional view, thereby increasing diagnostic sensitivity and specificity. These methods are explained in detail in the '355 and '322 patents, which were previously described and incorporated in as reference.

The invention reveals measurements of real-time spatiotemporal dynamics. Depending on the implementation, an image of dynamic optical properties of scattering medium such as, but not limited to, the vasculature of the human body in a cross-sectional view is provided. The technology employs low cost, compact instrumentation that uses non-damaging near infrared optical sources and features several alternate imaging heads to permit investigation of a broad range of anatomical sites.

In another implementation, the principles of the present invention can be used in conjunction with contrast agents such as absorbing and fluorescent agents. In another variant, the present invention allows tie cross-sectional measurements of changes in optical properties due to variations in temperature. The advantage of this variant is seen, but not restricted to, the use of monitoring cryosurgery.

A system using the modified instrumentation and described methods of the instant invention is capable of producing cross-sectional images of real-time events associated with vascular reactivity in a variety of tissue structures (e.g., limbs, breast, head and neck). Such measurements permit an in-depth analysis of local hemodynamic states that can be influenced by a variety of physiological manipulations, pharmacological agents or pathological conditions. Measurable physiological parameters include identification of local dynamic variations in tissue blood volume, blood oxygenation, estimates of flow rates, and tissue oxygen consumption. It is specifically noted that measurements of several locations on the same medium can be taken. For example, measurements may be taken of the leg and arm areas of a patient at the same time. Correlation of data between the different locations is available using the methods described herein.

The invention also provides both linear and non-linear time series analysis to reveal site specific functionality of the various components of the vascular tree. Thus the response characteristics of the major veins, arteries and structures associated with the microcirculation can be evaluated in response to a range of stimuli.

Fast data collection methods are particularly helpful because there are many disease states with specific influences on the spatial-dynamic properties of vascular responses. Accordingly, it is understood that significantly greater contrast mechanisms are definable, with much greater diagnostic sensitivity. This is accomplished by collecting and evaluating data in the time domain. These results are not available by performing static imaging studies.

The importance of dynamic properties follows directly from an understanding of the well known physiological reactivity of the vascular system. Control of the peripheral vasculature is mediated by neural, humoral and metabolic factors. Neural control is principally through autonomic activity. The details of these properties are well known to many, and can be found in any one of several medical physiology texts. Loss of autonomic control occurs in a variety of disease processes, especially in diabetes. Invariably, this loss of control will adversely influence local perfusion states. The current invention has the capacity to directly evaluate the concept known as vascular sufficiency. This tern takes into account the fact that, among its many roles, the vasculature is uniquely responsible for the delivery of essential nutrients to tissue, in particular, oxygen, and for the removal of metabolic waste products. Imbalances between supply and demand lead to relative hypoxic states, which often are clinically significant.

FIG. 1 illustrates one embodiment of the invention. Shown is a system 100 comprising medium 102. The medium can be any medium in which the propagation of the used source energy is strongly affected by scattering.

From a source module 101 energy is directed to the medium 102 from which the exiting energy is measured by means of detector 106, further discussed below. As previously discussed, there is a variety of sources, media, and detectors that may be used with the principles of the present invention. The following is a discussion of a sampling of such elements with the intention to describe how the invention is realized. In no way are these examples meant, nor do they intend to limit the invention to these implementations. A variation of elements as described herein may also utilize the principles of the present invention.

In one implementation, measurements of dynamics in the optical properties of the medium is accomplished by using optical source energy and performing rapid detection of the acoustic energy created by absorption processes in the medium. This can be implemented using both pulsed and harmonic modulated light sources, the latter allowing for lock-in detection. Detectors can be, but are not limited to, piezo-electric transducers such as PZT crystals or PVDF foils.

In another variant, a timing and control facility 104 is used to coordinate source and detector operation. This coordination is further described below. A device 116 provides acquisition and storage of the data measured by the detector 106. Depending on the implementation, control and timing of the system's components is provided by a computer, which includes a central processor unit (CPU), volatile and non-volatile memory, data input and output ports, data and program code storage on fixed and removable media and the like. Each main component is described in greater detail below.

Figure 2:
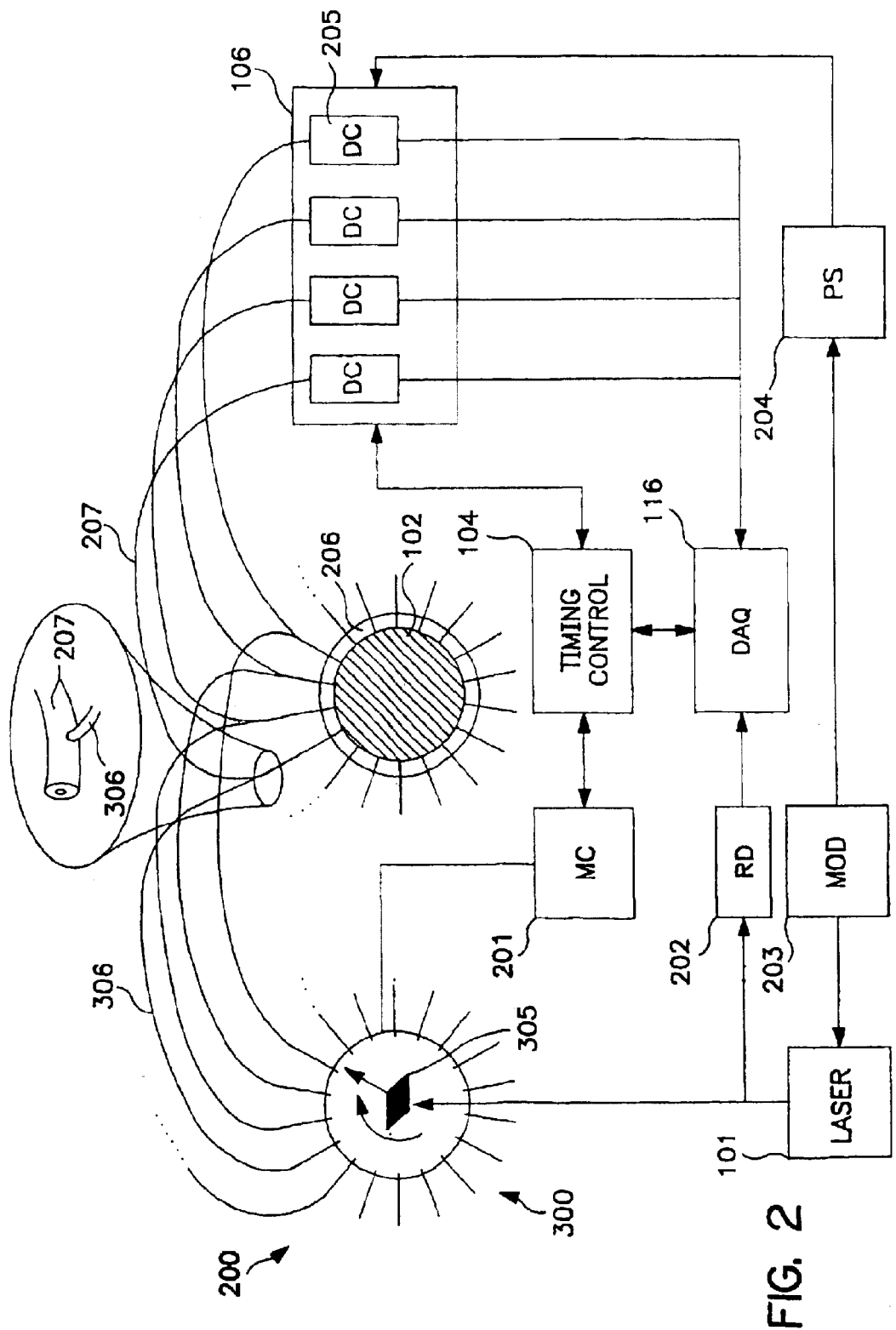
FIG. 2 is a block diagram illustrating one implementation of the system in FIG. 1.

FIG. 2 illustrates another implementation of a preferred embodiment of the present invention. Shown is a system and method that incorporates at least one wavelength measurement. Depending upon the implementation, this measurement is accomplished by alternately coupling light from diode lasers into transmitting fibers arranged in a circular geometry.

Referring again to FIG. 2, a system 200 includes an energy source, which in this implementation includes one or more laser 101. A reference detector 202 is used to monitor the actual output power of laser 101 and is coupled to a data acquisition unit 116. Such laser may be a laser diode in the NIR region. The laser is intensity modulated by a modulation means 203 for providing means of separation of background energy sources such as daylight. The modulation signal is also sent to a phase shifter 204 whose purpose is described further below. The light energy generated by the laser 101 is directed into an optical de-multiplexing device 300 further discussed in detail below. Using a rotating mirror 305, the light is directed into one of several optical source fiber bundles 306 that are used to deliver the optical energy to the medium 102. To provide good optical contact and measurement fidelity, one of several possible imaging heads 206 as described further below is used. A motor controller 201 is coupled to the de-multiplexing device 300 for controlling the motion of the rotating mirror 305. The motor controller 201 is also in communication with a timing control 104 for controlling the timing of the motion of mirror 305.

The measuring head 206 comprises the common end of a bifurcated optical fiber bundle, whose split ends are formed by the source fiber bundle 306 and detector fiber bundle 207. Source fiber bundle 306 and detector fiber bundle 207 form a bulls eye geometry at the common end with the source fiber bundle in the center. In other embodiments, source and detector bundles are arranged differently at the common end (e.g., reversed geometry or arbitrary arrangement of the bundle filaments). The common end of a bifurcated optical fiber bundle, preferably comes in contact with the medium, however, this embodiment is not limited to contact with the medium. For example, the common ends may simply be disposed about the medium. The signal is transmitted from the detector fiber bundle 207 to a detector unit 106 that comprises at least one detector channel 205 further described herein. The detector channel 205 is coupled to the data acquisition unit 116 and the timing control unit 104. Depending on the implementation, a phase shifter 204 may or may not be used, and is coupled to the detector unit 106 for the purposes of providing a reference signal for the purposes of filtering the signal received from bundle 207.

Figure 3:
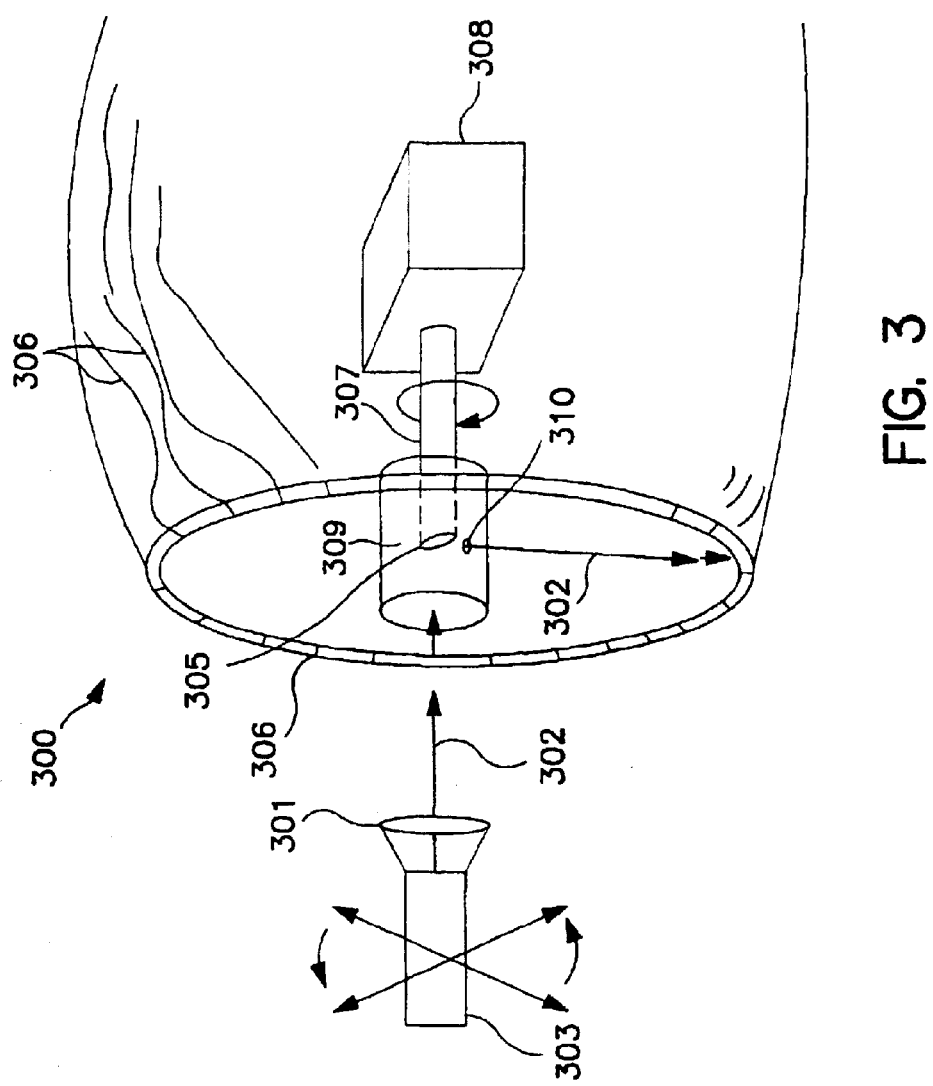
FIG. 3 is a perspective view of a servo-motor apparatus useful in this invention to illuminate a number of fiber bundles with a single energy source.

Depending on the implementation, illustrated in FIG. 3 is a device for the measurement of the dynamic properties of a scattering medium. This measurement is performed by sequentially reflecting light 302 off of a rotatable front surface mirror 306, mounted at a 45 degree angle to the incident source, into source fibers 306 arranged in a circular geometry about the rotating optic. The rotation is done by a motor 308 with a shaft 307 to which the mirror is attached. This embodiment has an advantage of enabling fast switching among the transmitting fibers. In particular, it provides the ability to introduce beam shaping optics between the reflective mirror and transmitting fibers thereby allowing fine adjustment of the illumination area available for coupling into the fibers. This is useful because it allows independent adjustment of the rotation speed of the reflective optic (i.e., switching speed), and the illumination time allowed for each transmitting fiber bundle. Thus, a range of illumination frequencies can be employed while allowing fine adjustment of the illumination time at each source position to permit collection of data having a suitable signal-to-noise ratio.

Light from laser 101 is transmitted to unit 300 by means of transmitting optics 303 including, but not limited to, fiber optics and free propagating beams. Further beam shaping optics 301 may be used to optimize in coupling efficiency into the transmitting fibers. Units 303 and 301 are under mechanical fine adjustment in their position with respect to the mirror 309.

Motor 308 is operated under control of motion control 201 to allow for precise positioning and timing. By this means, it is possible to operate the motor under complex motion protocols such as in a start-stop fashion where the motor stops at a desired location thereby allowing the stable coupling of light into a transmitting fiber bundle. After the measurement at this source location is performed, the motor moves on to the next transmitting fiber. Motion control is in two-way communication with the timing control 104 thereby allowing precise timing of this procedure. Motion control allows the assignment of relative and/or absolute mirror positions allowing for precise alignment of the mirror with respect to the physical location of the fiber bundle. The mirror 306 is surrounded by a cylindrical shroud 309 in order to shield off stray light to prevent cross-talk. The shroud comprises an aperture 310 through which the light beam 302 passes toward the transmitting fiber. It is recognized and incorporated herein other schemes which may be used,(e.g., use of a fiber-optic switching device) to sequentially couple light into the transmitting fibers.

In an equivalent embodiment, fast switching of source positions is accomplished by using a number of light sources, each coupled into one of the transmitting fibers 306 which can be turned on and of each independently by electronic means.

The device employs the servo-motor control system 308 in FIG. 3 with beam steering optics, described above, to sequentially direct optical energy emerging from the source optics onto about 1 mm diameter optical fiber bundles 306, which are mounted in a circular array in the multiplexing input coupler 300. The transmitting optical fiber bundles 306, which are typically 2–3 meters in length are arranged in the form of an umbilical and terminate in the imaging head 206.

Depending on the implementation, the apparatus of the present invention required for time-series imaging, employs the value of using a geometrically adaptive measurement head or imaging head. The imaging head of the present invention provides features that include, but are not limited to, 1) accommodating different size targets (e.g., breast); 2) stabilizing the target against motion artifacts; 3) conforming the target to well-defined geometry; and 4) to provide exact knowledge of locations for sources and detectors. Stability and a known geometry both contribute to the use of efficient numerical analysis schemes.

There are several different embodiments of the imaging head for data collection that may utilize the principles of the present invention. For example the use of an iris imaging head previously disclosed in the '322 and '355 patents, which are incorporated by reference in this disclosure, may be used with the principles of the present invention.

Described below are two exemplary imaging heads with the understanding that the invention may or may not use any type of imaging head, and if an imaging head is used, it would provide the features previously described.

Figure 4:
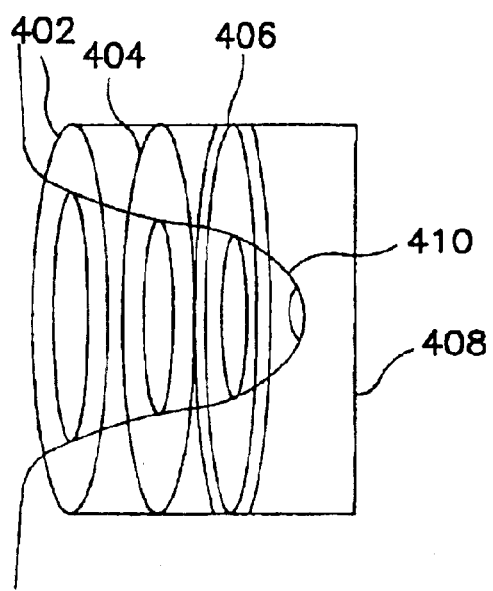
FIG. 4 is a schematic illustration of the disposition for examining human tissue such as a human breast.

As illustrated in FIG. 4, the iris unit can be employed as a parallel array of irises 402, 404, 406 enabling volume imaging studies. FIG. 4 illustrates how this can be configured for studying a medium 410, in this example a human breast, using an imaging head 408. As described previously, the medium used in the present invention can be any medium, which allows scattering of energy.

Figure 5:
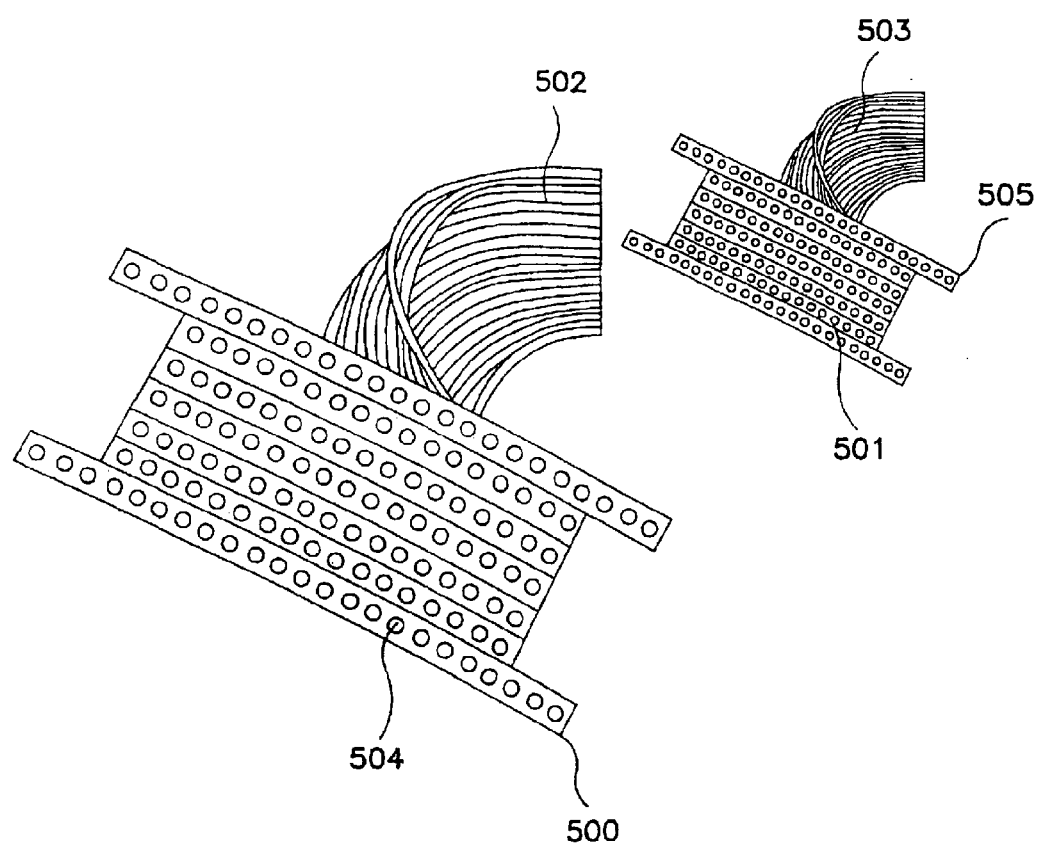
FIG. 5 is a schematic illustration of a planar imaging head useful in one embodiment of the invention.

In one implementation, the imaging head illustrated in FIG. 5 is a flexible pad configuration. This planar imaging unit functions as a deformable array and is well suited to investigate body structures too large to permit transmission measurements (e.g., head and neck, torso, and the like). Using this type of imaging head, optical measurements are made in a back-reflection mode. Optical fiber bundles 502 originating from the optical multiplexing input coupler 112 (described elsewhere) terminate at the deformable array or flexible pad 500. The pad can be made of any flexible material such as black rubber or the like. The optical fiber bundles may be bifurcated and have ends 504 that both transmit and receive light. More than one pad may or may not be used, although an additional pad is not necessary for the purpose of the present invention, or for measurement application to other portions of the medium or to the same medium. For example, in the case of a breast exam, both pads maybe applied to the same breast having one pad above and one pad below the breast. In addition, one pad maybe applied to the right breast by having the pad deformed around the breast. Similarly, the other pad may be applied to the left breast. This configuration would allow both breasts to be examined at the same time. In addition, information may be correlation between the data collected from the two different members of the body. Again, the invention can be applied to other media and is not limited to portions of the human body. Thus, correlation between different media may be collected using this technique.

Figure 6:
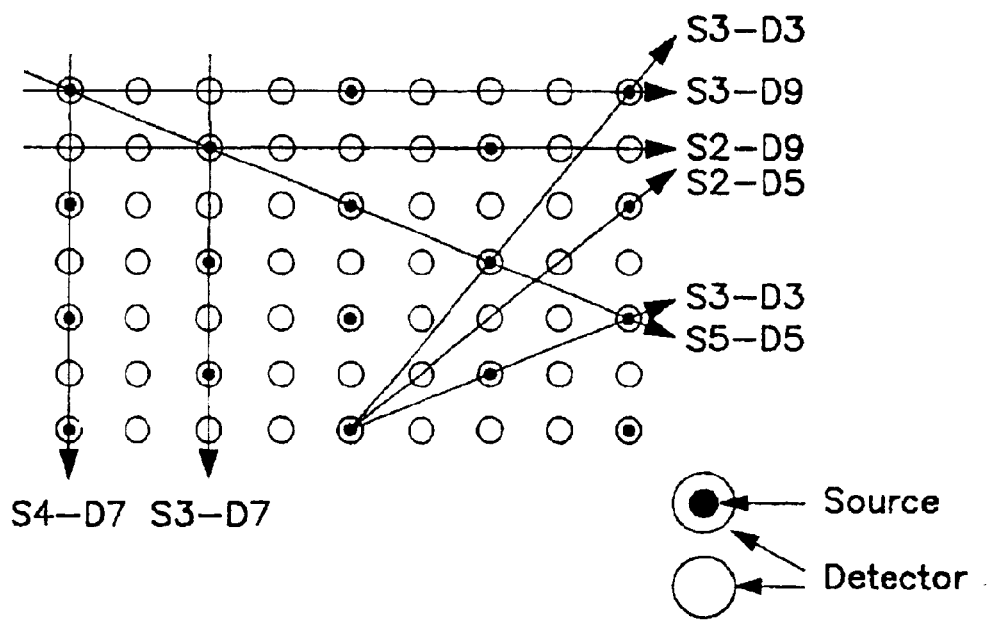
FIG. 6 is one embodiment for the source detector arrangement on the imaging head shown in FIG. 5.

As further shown in FIG. 5, the additional pad would have similar functions as the pad previously described and would have optical fiber bundles 503, flexible pad 505, and bifurcated optical fiber bundle ends 501 similar to the previous pad described. The array itself can be deformed to conform to the surface of a curved medium to be imaged (e.g. portion of the torso). The deformable array optical energy source and receiver design includes, depending on the implementation, a 7×9 array (63 total bundles) of optical fiber bundles as illustrated in FIG. 6. In one variant, each bundle is typically 3 mm in diameter. Depending on the implementation, eighteen (18) of the sixty-three (63) fiber bundles may be arranged in an array to serve as both optical energy sources or energy transmitters, and receivers to sequentially deliver light to a designated target and receive emerging optical energy. In this implementation, the remaining forty-five (45) fiber bundles act only as receivers of the emerging optical energy.

The geometry of the illumination array is not arbitrary. The design shown in FIG. 6 as an exemplary illustration has been configured, as have other implementations, to minimize the subsequent numerical effort required for data analysis while maximizing the source-density covered by the array. The fiber bundles are arranged in an alternating pattern as described by FIG. 6 and shown here with the symbols "X" and "0". In one implementation, a pattern of 00X000X00, X000X000X can be used on the imaging head. 'X' denotes a source/receiver fiber bundle, and '0' is a receiver only. FIG. 6 indicates 2D imaging planes formed by multiple source/detector positions along a line that can be used with this particular pattern. The labels refer to the numbers of sources/detectors found along those lines of optical fiber ends on the pad using the following nomenclature: "S" followed by a number indicates the number of source positions along that line; "D" followed by a number indicates the number of detection points along that line. For instance; "S3-D3" indicates an imaging plane formed by three source positions and three detection points. Basically, the design allows for the independent solution of two dimensional (2-D) image recovery problems from an eighteen (18) point source measurement. As a result, a composite three dimensional (3-D) image can be computed from superposition of the array of 2-D images oriented perpendicular to the target surface. Another advantage of this geometry is that it readily permits the use of parallel computational strategies without having to consider the entire volume under examination.

The advantage of this geometry is that each reconstruction data set is derived from a single linear array of source-detector fibers, thereby enabling solution of a 2-D problem without imposing undue physical approximations. The number of source-detector fibers belonging to an array can be varied. Scan speeds attainable with the 2-D array illustrated in FIG. 6 are the same as for other imaging heads with 2-D arrays since the scan speed depends only on the properties of the input coupler. Thus, faster scan speed are available for the creation of a 3-D image.

Figure 7:
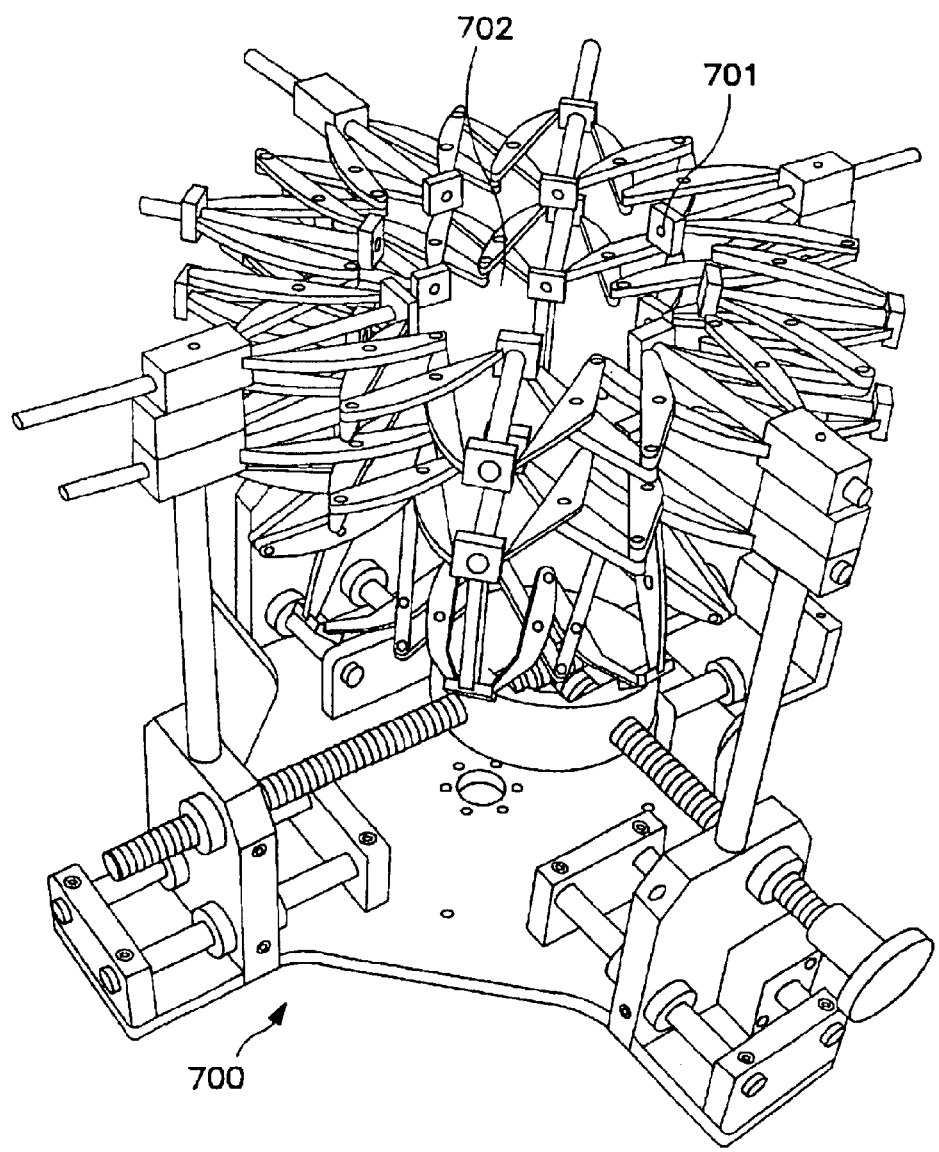
FIG. 7 is an illustration of a spherical imaging head useful in practicing the invention.

In another implementation, illustrated in FIG. 7, is an imaging head based on a "Hoberman" sphere geometry. In a Hoberman structure, the geometry is based on the intersection of a cube and an octahedron, which makes a folding polyhedron called a trapezoidal icosatetrahedron. This structure has been modified and implemented in a form of an imaging head of a hemispherical geometry. For many purposes of the instant invention, it is appropriate to use design features of smoothly varying surfaces based on the Hoberman concept of expanding structures. Depending on the implementation, other polygonal or spherical-type shapes may also be used with the principles of the present invention for other imaging head designs. Adjustment of the device in FIG. 7 causes uniform expansion or contraction, thereby always preserving a hemispherical geometry. Imaging head 700 illustrates one example of modification to the "Hoberman" geometry. A receptacle for the fiber bundles 701 is disposed about imaging head 700. Target volume 702 is where the medium would enter the imaging head in this implementation. This geometry is well suited for the investigation of certain tissues such as the female breast or the head. Depending on the implementation, attachment of optical fibers to the vertices of the hemisphere allows for up a seventeen (17) source by seventeen (17) detector measurement. The folding structure can be extended to accommodate a more "tear drop" or "bullet" shape of the target medium by attaching additional circular iris-like structures on top that expand and contract with the hemisphere. FIG. 7 shows the combination of the hemisphere with one top iris comprising receptacles for 8 additional fiber bundles leading to an overall number of 25 source by 25 detector positions at the main vertices for this configuration. More than one iris can be attached to the top of the hemisphere. The diameter of the additional top irises may or may not differ from the hemisphere diameter. The detectors or energy receivers may be disposed about the imaging head and the detectors are located on the inner aspect of the expanding imaging head. Additional fiber bundles can be attached to the interlocking joints, permitting up to a 49 source by 49 detector measurement for the hemisphere only and up to 16 source/detector positions per added iris.

Depending on the implementation, light collected from the target medium is measured by using any of a number of optical detection schemes. One embodiment uses a fiber-taper, which is bonded to a charged coupled detector (CCD) array. The front end of the fiber taper serves to receive light exiting from the collection fibers. These fibers are preferably optical fibers, but can be any means that allows the transmission and reception of signals. The back end of the fiber taper is bonded to a 2-D charge-coupled-detector (CCD) array. In practice, use of this approach generally will require an additional signal attenuation module.

An alternate detection scheme employs an array of discrete photo detectors, one for each fiber bundle. This unit can be operated in a phase lock mode thereby allowing for improved rejection of ambient light signals and the discrimination of multiple simultaneously operated energy sources.

In another embodiment, in order to fulfill the demands posed by the desired physiological studies on the instrument, the following features characterize the detector system: scalable multi-channel design (up to 32 detector channels per unit); high detection sensitivity (below 10 pW); large dynamic range ($1:10^6$ minimum); multi-wavelength operation; ambient light immunity; and fast data acquisition (order of 100 Hz all-channel simultaneous capture rate).

To achieve this, the detector system uses photodiodes and a signal recovering technique involving electronic gain switching and phase sensitive detection (lock-in amplification) for each detector fiber (in the following referred to as detection or detector channels) to ensure a large dynamic range at the desired data acquisition rate. The phase sensitive signal recovery scheme not only suppresses electronic noise to a desired level but also eliminates disturbances given by background light and allows simultaneous use of more than one energy source. Separation of signals from simultaneously operating sources can be achieved, as long as the different signals are encoded in sufficiently separated modulation frequencies. Since noise reduction techniques are based on the reduction of detection bandwidth, the system is designed to maintain the desired rate of measurements. In order to achieve a timing scheme that allows simultaneous readout of the channels, a sample-and-hold circuit (S/H) is used for each detection channel output. The analog signals provided by the detector channels are sampled, digitized and stored using the data acquisition system 116. One aspect is the flexibility and scalability of the detection instrument. Not only are the detector channels organized in single, identical modules, but also the phase detection stages, each containing two lock-in amplifiers, are added as cards. In this way, an existing setup can easily be upgraded in either the number of detector channels and/or the number of wavelengths used (up to four) by cloning parts of the existing hardware.

Figure 8:
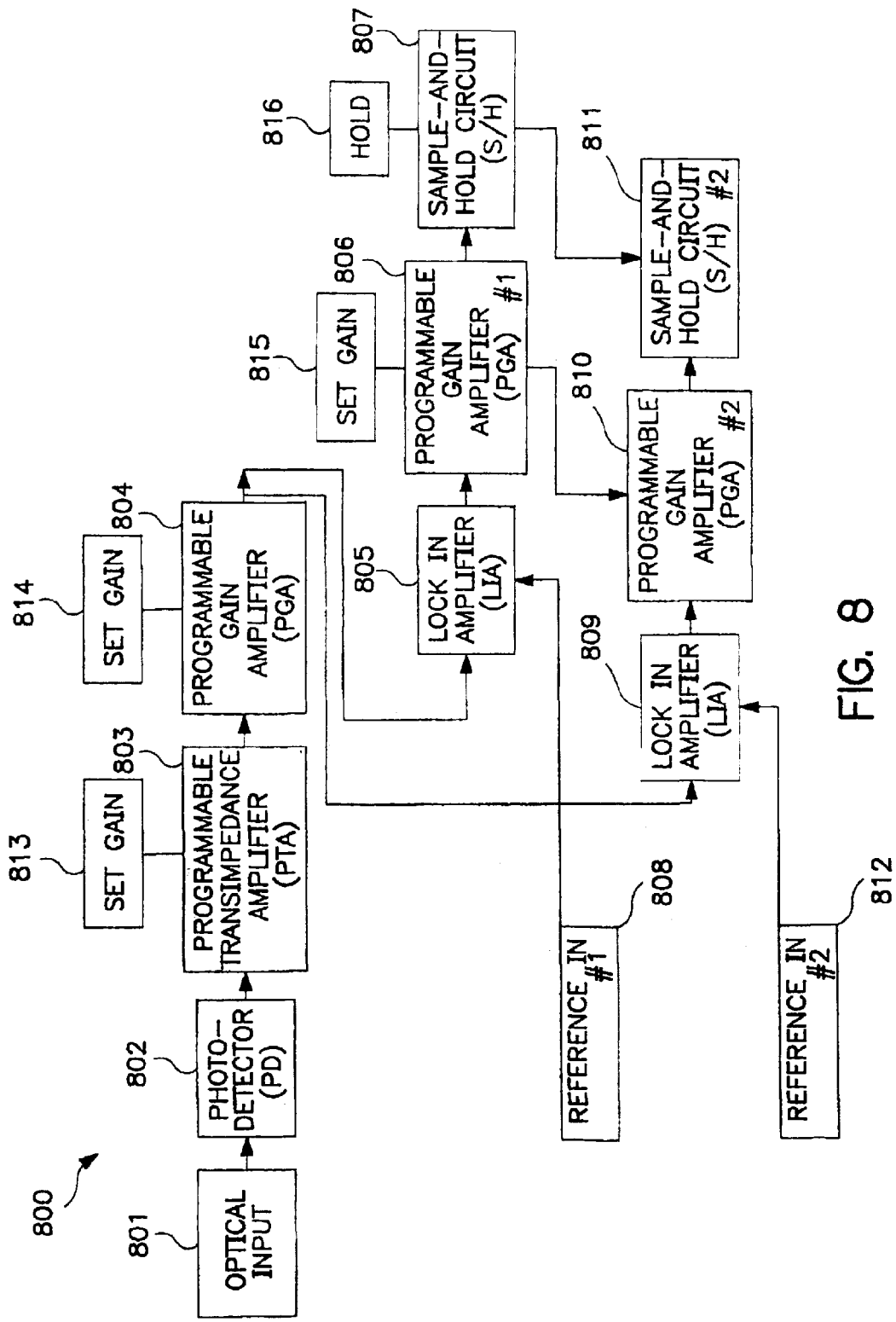
FIG. 8 is a block diagram of a detector channel useful in practicing the invention.

FIG. 8 shows the block diagram of one implementation of a detector channel. In this implementation, two energy sources are used. After detecting the light at the optical input 801 by a photo detector 802 the signal is fed to a transimpedance amplifier 803. The transimpedance value of 803 is externally settable by means of digital signals 813 (PTA= Programmable Transimpedance Amplifier). This allows the adaptation to various signal levels thereby increasing the dynamic range of the detector channel. The signal is subsequently amplified by a Programmable Gain Amplifier (PGA} whose gain can be set externally by means of digital signals 814. This allows for additional gain for the lowest signal levels (e. g., in one implementation pW-nW) thereby increasing the dynamic range of the detector channel.

In one embodiment, at least one energy source is used and the signal is sent to at least one of lock-in amplifiers (LIA) 805, 809. Each lock-in amplifier comprises an input 808,812 for the reference signal generated by phase shifter 204 from FIG. 2. After lock-in detection, the demodulated signal is appropriately boosted in gain by means of a programmable gain amplifier (PGA) 806, 810 in order to maximize noise immunity during further signal transmission and to improve digital resolution when being digitized. The gain of PGA 806, 810 is set by digital signals 815.

At each output, a sample-and-hold circuit (S/H) 807, 811 is used for freezing the signal under digital timing by means of signal 816 for purposes described herein.

In one embodiment, the signal 815 is sent to PGA 806,810 in parallel. In one embodiment, the signal 816 is sent to 807,811 in parallel.

As previously illustrated in FIG. 1, the analog signal provided by each of the channel outputs is sampled by a data acquisition system 116. In one embodiment, PC extension boards might be used for this purpose. PC extension boards also provide the digital outputs that control the timing of functions such as gain settings and sample-and-hold.

Figure 9:
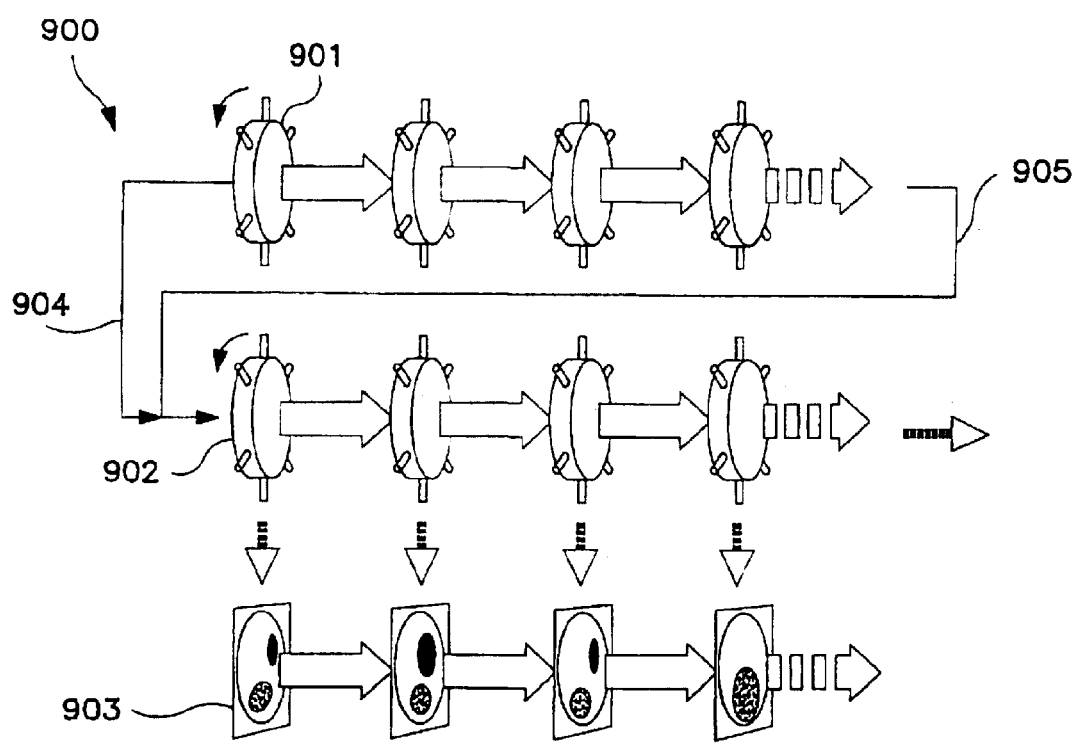
FIG. 9 is a graphical representation of one implementation of a timing scheme used in the system of FIG. 1.

As previously noted, timing is crucial in order to provide the desired image capture rate and to avoid false readings due to detector-to-detector time skew. FIG. 9 shows one improvement of the invention over other timing schemes. With systems not comprising fast adaptable gain settings (such as some CCD based systems), a schedule according to 905 has to be implemented. The implementation in FIG. 9 illustrates one use of a silicon photo-diode in process 904, which can be replaced by various detectors previously mentioned. A time series of data is acquired for a fixed source position. After finishing this task, the source is moved 902 with respect to the target 901 and another series of data is collected. Measurements are performed in this fashion for all source positions. Every image 903 of the resulting time series of reconstructed images is reconstructed from data sets merged together from the data for each source position. This schedule does not allow real-time capture of all physiologic processes in the medium and therefore only applies to certain modes of investigation. Although we are aware of the use of such schemes, e.g., when monitoring responses on repeatable maneuvers, the timing scheme for the invention very much improves on this situation.

Because the invention allows for fast source switching and large dynamic range and high data acquisition rates, a schedule indicated by 904 is performed. Here, the source position is switched fast compared to the dynamic features of interest and instantaneous multi-channel detection is performed at each source position. Images 903 are then reconstructed from data sets, which represent an instant state of the dynamic properties of the medium. Only one time series of full data sets (i. e., all source positions and all detector positions) is being recorded. Real time measurement of fast dynamics (e. g., faster than I Hz) of the medium is provided by the invention.

Figure 10:
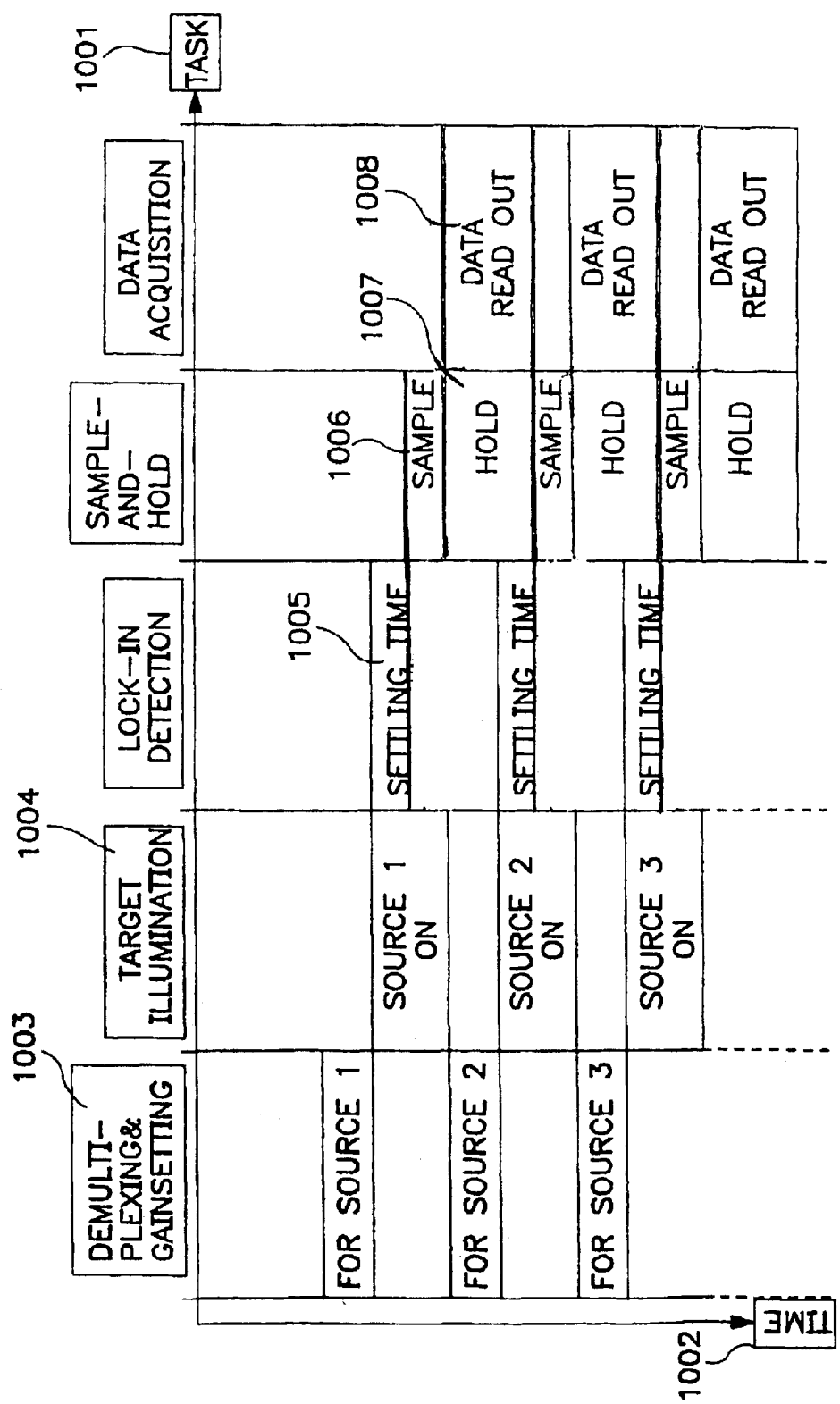
FIG. 10 is a diagram illustrating the sequence of certain events in a multiple channel embodiment of the invention.

FIG. 10 shows one embodiment of a detailed schedule and sequence of the system tasks 1001 involved in collecting data at a source position and the proceeding of this process in time 1002. Task 1003 is the setting of the optical de-multiplexer to a destined source position and setting the detectors to the appropriate gain- settings. The source position is illuminated for a period of time 1004, during which the lock-in amplifiers settle 1005. After the time it takes the S/H to sample the signal 1006, the signal is held for a period of time 1007, during which all channels are read out by the data acquisition. It is worthwhile noticing that during reading out the S/H, other tasks, like moving the optical source, setting the detector gains for the new source position, and settling of the lock-in, are being scheduled. This increases greatly the achievable data acquisition rate of the instrument.

Figure 11:
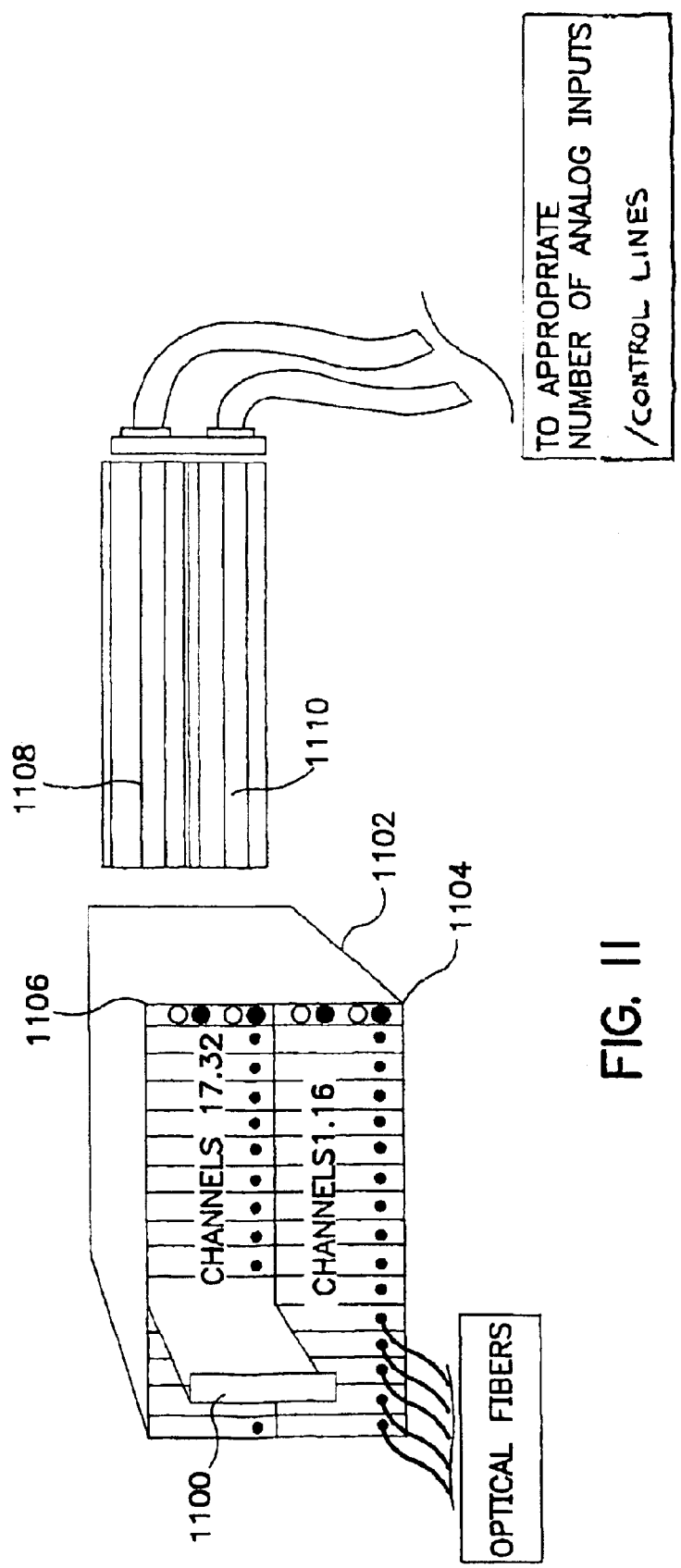
FIG. 11 is a schematic illustration of the physical arrangement of multiple detector channels used in a preferred embodiment of the invention.

This concept of a modular system is further illustrated in FIG. 11. Up to thirty-two (32) detector modules 1100 (each with 2 lock-in modules each for two modulation frequencies) are arranged using an enclosure 1102. The cabinet also can carry up to two phase shifting modules 1104, 1106, each containing two digital phase shifter under computer control. The ability to adjust the reference phase with respect to the signal becomes necessary since unavoidable phase shifts in the signal may lead to non-optimum lock-in detection or can even result in a vanishing output signal. Organization of data, power supply and signal lines is provided by means of two back planes 1108, 1110

Depending on the implementation, the detector system design illustrated in FIG. 8 allows one cabinet to operate at a capacity of 32 detectors with four different sources requiring 128 analog to digital circuit (ADC)-board input channels. The upper 1108 and the lower 1110 back plane are of identical layout and have to be linked in order to provide the appropriate distribution of supply-, control- and signal voltages. This is achieved using a 6U-module fitting both planes from the backside, that provides the necessary electric linking paths, and interfaces for control- and signal lines.

Figure 12A:
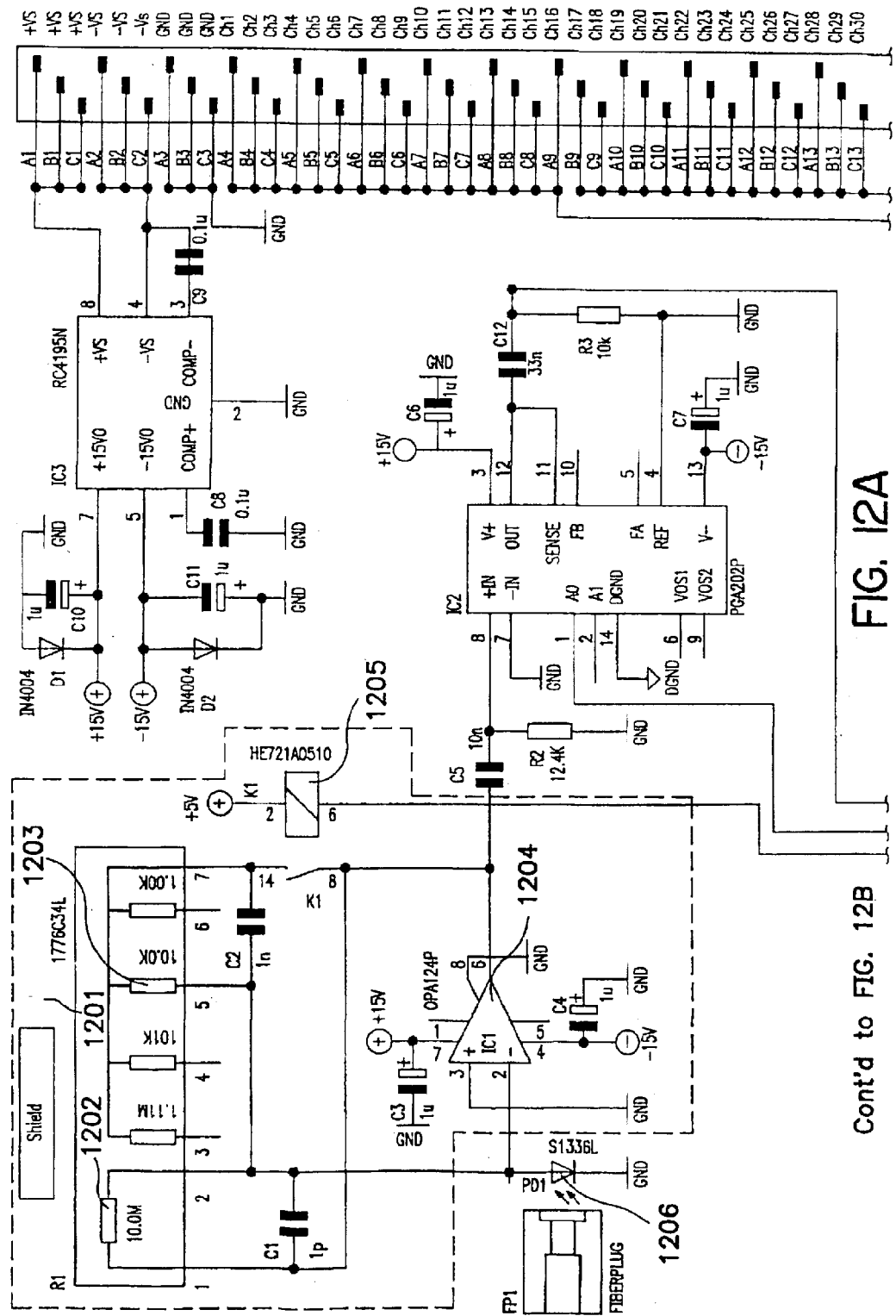
FIG. 12 is a circuit diagram of one detector channel used in FIG. 11.
Figure 12B:
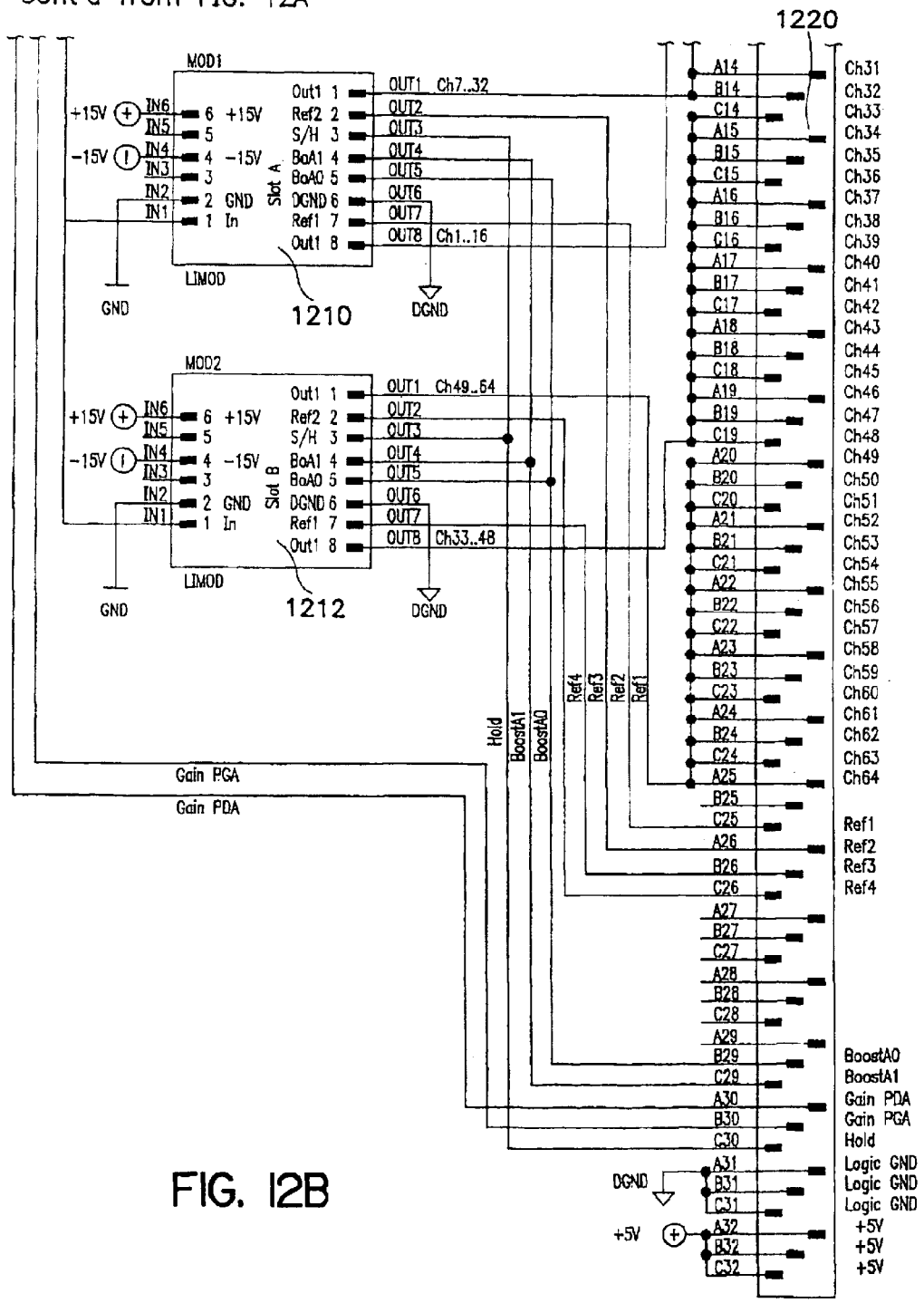

FIG. 12 shows the schematic of one implementation of a channel module. In this implementation, a silicon photodiode 1206 is used as the photo-detector. A Programmable Transimpedance Amplifier (PTA) 1201 is formed by an operational amplifier 1204, resistors 1201 and 1202 and an electronic switch 1205, the latter of which is realized using a miniature relay. Other forms of electronic switches such as analog switches might be used. Relay 1205 is used to connect or disconnect 1203 from the circuit thereby changing the transimpedance value of 1201. A high-pass filter (R2, C5) is used to AC-couple the subsequent programmable gain instrumentation amplifier IC2 (Burr Brown PGA202) in order to remove DC offset. The board-to-board connectors for the two lock-in-modules are labeled as "slot A" 1210 and "slot B" 1212. The main connector to the backplane is a 96-pole DIN plug 1220.

Figure 13A:
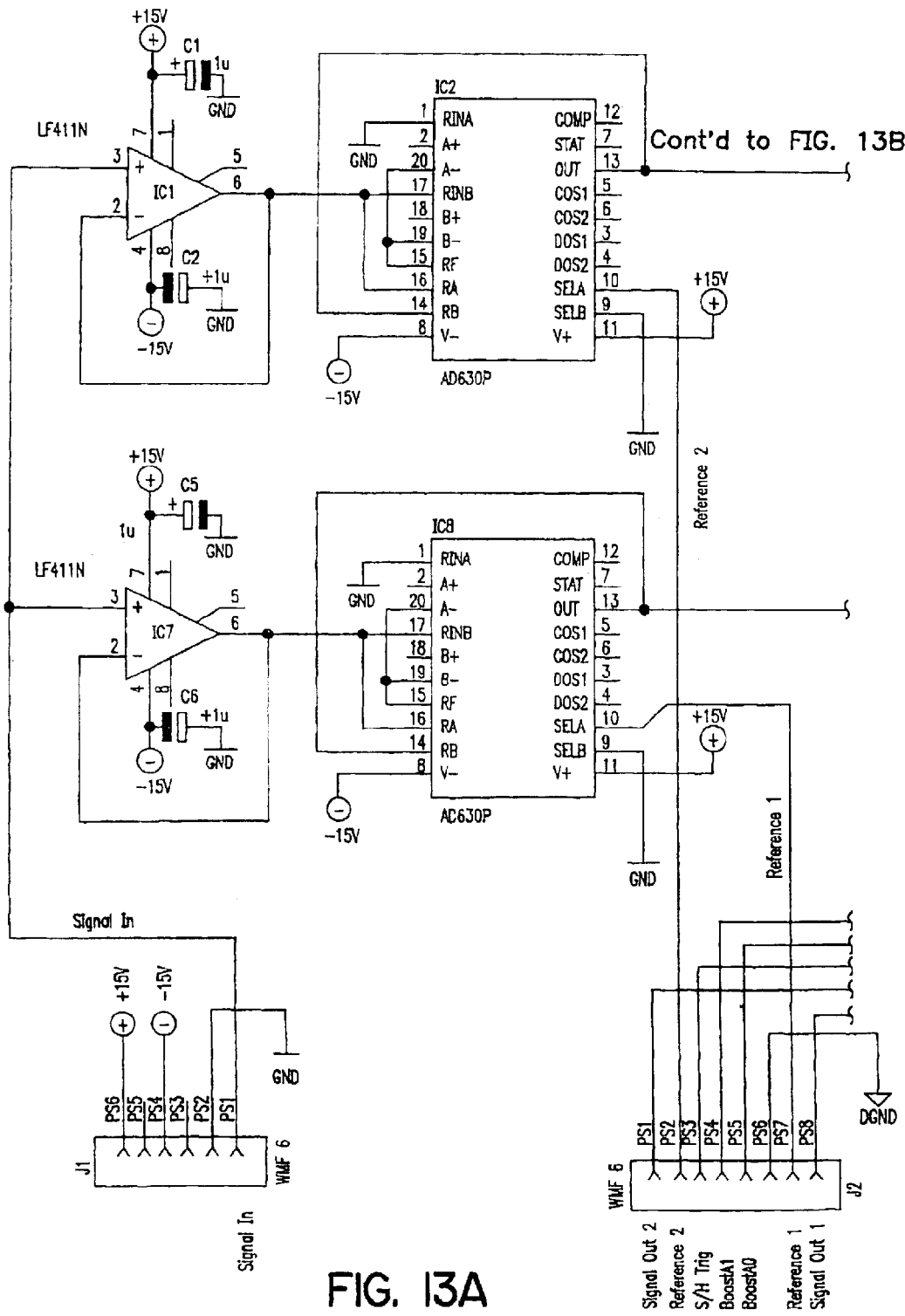
FIG. 13 is a circuit diagram of one implementation of the lock-in module used in FIG. 12.

FIG. 13, illustrates the electric circuit of the lock in modules 1210, 1212. The signal is subdivided and passed to two identical lock-in-amplifiers, each of which gets one particular reference signal according to the sources used in the experiment. The signal is first buffered IC1, IC7 (AD LF 111) and then demodulated using an AD630 double-balanced mixer IC2, IC8.

In order to remove undesired AC components, the demodulated signal passes through an active 4-pole Bessel-type filter IC3, IC4, IC9, IC10 (Burr Brown UAF42). A Bessel-type filter has been chosen in order to provide fastest settling of the lock-in amplifier for a given bandwidth. Since a Bessel-filter shows only slow stopband-transition, a 4-pole filter is being used to guarantee sufficient suppression of cross talk between signals generated by different sources (i.e. of different modulation frequency). The filter has its 3 dB point at 140 Hz, resulting in 6 ms settling time for a step response (<1% deviation of actual value). The isolation of frequencies separated by 1 kHz is 54 dB. The filters are followed by a programmable gain amplifier IC5, IC 11, whose general function has been described above. The last stage is formed by a sample-and-hold chip (S/H) IC6, IC12 (National LF398).

In another implementation, the phase sensitive detection can be achieved with digital methods using digital signal processing (DSP) components and algorithms. The advantage of using DSP with the principles of the present invention is improved electronic performance and enhanced system flexibility.

In another implementation, an analog-to-digital converter is used for each detector channel thereby improving noise immunity of the signals.

Although illustrative embodiments have been described herein in detail, those skilled in the art will appreciate that variations may be made without departing from the spirit and scope of this invention. Moreover, unless otherwise specifically stated, the terms and expressions used herein are terms of description and not terms of limitation, and are not intended to exclude any equivalents of the system and methods set forth in the following claims.

What is claimed is:

1. A system for use in tomographic imaging of a scattering medium, comprising:
   a plurality of energy sources, each energy source emitting a respective signal for imaging the scattering medium;
   wherein the plurality of energy sources emit their respective signals sequentially and the respective signals are scattered by the scattering medium and emerge from the scattering medium; and
   a plurality of detectors for detecting the respective signals that emerge from the scattering medium for use in measuring dynamic properties of the scattering medium in a time series of images using optical tomography.

2. The system of claim 1, further comprising:
   an imaging head on which the energy sources and the detectors are arranged;
   wherein the energy sources and the detectors are arranged in a plurality of linear arrays to enable reconstruction of a corresponding plurality of 2-D images of the scattering medium.

3. The system of claim 1, further comprising means for adjusting a gain of at least one of the detectors, when the at least one of the detectors detects the respective signal from one of the energy sources, according to a position of the one of the energy sources.

4. The system of claim 1, further comprising at least one sample-and-hold circuit for freezing the respective signals detected by the detectors to enable a simultaneous readout of the respective signals detected by the detectors.

5. The system of clam 1, wherein the energy sources include at least one of a non-laser optical source LED, high-pressure incandescent lamp, laser diode, solid state laser, titanium-sapphire laser, ruby laser, dye laser, electromagnetic source acoustic energy source, acoustic energy produced by optical energy, optical energy, and combinations thereof.

6. The system of claim 1, wherein data acquisition from the detectors is at a rate of about 100 Hz.

7. The system of claim 1, wherein the energy sources include near infra red laser diodes that transmit multiple wavelengths.

8. The system of claim 1, wherein the detectors include at least one of a photo-diode, PIN diode, Avalanche photodiode, charge coupled device, charge inductive device, photo-multiplier tube, multi-channel plate, acoustic transducer, and any combinations thereof.

9. The system of claim 3, further including a sample-and-hold circuit coupled to the means for adjusting that allows simultaneous readout of the respective signals detected by the detectors.

10. A system for use in optical tomographic imaging of a scattering medium comprising:
    at least one energy transmissive fiber bundle coupled to at least one energy source;
    the at least one energy transmissive fiber bundle emitting energy from the at least one energy source, and detecting the energy after it is scattered by the scattering medium;
    an imaging head for holding the at least one energy transmissive fiber bundle; and
    a detection system for collecting data regarding the optical dynamic properties of the scattering medium from the detected energy;

wherein the imaging head undergoes uniform expansion and contraction to accommodate different size scattering mediums.

11. The system of claim 10, wherein the at least one energy transmissive fiber bundle is bifurcated to both emit and detect energy.

12. The system of claim 10, wherein the imaging head comprises a folding sphere or polygon.

13. The system of claim 10, wherein the at least one energy transmissive fiber bundle comprises a plurality of energy transmissive fiber bundles disposed about the imaging head.

14. A method of imaging a scattering medium using optical tomographic imaging, comprising:
(a) exposing the scattering medium to energy from a plurality of energy sources that sequentially emit the energy; and
(b) detecting the energy, via a plurality of detectors, after the energy has been scattered by the scattering medium for use in measuring dynamic properties of the scattering medium in a time series of images using optical tomography.

15. The method of claim 14, wherein the scattering medium comprises vascular tissue.

16. The system of claim 1, wherein the respective signals emitted by the energy sources comprise optical energy of at least two different intensity modulated wavelengths of energy.

17. The system of claim 16, further comprising a filter for separating signals corresponding to a wavelength of the intensity modulated energy.

18. The system of claim 1, wherein the respective detectors comprise respective fibers coupled to respective optical energy detectors.

19. An imaging head, comprising:
a pad;
a plurality of source means for delivering optical energy to a medium; and
a plurality of detector means for detecting optical energy emerging from the medium; wherein:
the source means and detector means are attached to the pad in a plurality of rows and columns wherein the plurality of source means are arranged to form at least two unique imaging planes, an imaging plane being between defined by a plane substantially perpendicular to the pad and passing through at least two source means and one detector means; and
the source means and detector means are arranged in first and second patterns in alternating rows, the first pattern comprising one source means followed by three detector means followed by one source means followed by three detector means, and the second pattern comprising a shifted version of the first pattern.

20. The imaging head of claim 19, wherein the source means comprise fibers coupled to an optical energy source.

21. The imaging head of claim 19, wherein the source means comprise optical energy sources.

22. The imaging head of claim 19, wherein the source means comprise laser diodes.

23. The imaging head of claim 19, wherein the detector means comprise fibers coupled to optical energy detectors.

24. The imaging head of claim 19 wherein the detector means comprise optical energy detectors.

25. The imaging head of claim 19 wherein the detector means comprise photodiodes.

26. The system of claim 1, wherein the energy sources and the detectors are arranged in an illumination array that is configured to minimize subsequent numerical effort required for data analysis and maximizing source density covered by the illumination array.

27. The system of claim 26, wherein the energy sources and the detectors are arranged in the illumination array to enable three dimensional images to be computed from super positioning of two dimensional images.

28. The detection system of claim 1, wherein the detectors further detect fluorescence radiation excited by the energy sources.

29. The detection system of claim 1, wherein the detectors further detect acoustic energy produced in the scattering medium by the energy sources.

30. The system of claim 10, wherein the at least one energy transmissive fiber bundle terminates inside the scattering medium.

31. The method of claim 14, further including the step of evaluating the dynamics in an industrial mixing process for at least one of a gas and a liquid according to the detected energy.

32. The method of claim 14, further including evaluating dynamics in a foggy atmosphere according to the detected energy.

33. The method of claim 14, further including evaluating dynamics in oceans or water masses according to the detected energy.

34. The system of claim 1, further comprising means for adjusting a gain of at least one of the detectors according to respective positions of the energy sources.

35. The system of claim 1, further comprising means for adjusting respective gains of the detectors according to respective positions of the energy sources.

36. The system of claim 1, wherein distances between source-detector pairs of the energy sources and the detectors vary over a distance of at least about 5 cm.

37. The system of claim 1, wherein the scattering medium comprises a large tissue structure.

38. The system of claim 1, further comprising a data acquisition unit for reconstructing the time series of images of the scattering medium based on the respective signals detected by the detectors.

39. The system of claim 2, wherein there are varying numbers of pairs of the energy sources and the detectors in the linear arrays.

40. The system of claim 3, wherein the means for adjusting comprises a programmable gain amplifier.

41. The system of claim 10, wherein the imaging head undergoes uniform expansion and contraction while preserving a hemispherical geometry to accommodate different size scattering mediums.

42. The system of claim 10, wherein the imaging head includes a target volume through which the scattering medium enters the imaging head.

43. The system of claim 10, wherein detector fibers of the at least one energy transmissive fiber bundle are located on an inner aspect of the imaging head.

44. The system of claim 13, wherein the imaging head comprises a Hoberman sphere, about which the plurality of energy transmissive fiber bundles are disposed.

45. The system of claim 13, wherein the plurality of energy transmissive fiber bundles are attached to vertices of a hemisphere of the imaging head.

46. The system of claim 13, wherein the plurality of energy transmissive fiber bundles are attached to interlocking joints of the imaging head.

47. The method of claim 14, further comprising adjusting respective gains by which the energy is detected by the detectors according to respective positions of the energy sources.

48. The method of claim 14, wherein the energy comprises near infra-red light.

49. The method of claim 14, wherein distances between source-detector pairs of the sources and the detectors vary over a distance of at least about 5 cm.

50. The method of claim 14, wherein the scattering medium comprises a large tissue structure.

51. The system of claim 1, further comprising:

an imaging head on which the energy sources and the detectors are arranged;

wherein the energy sources and the detectors are arranged in a plurality of linear arrays to enable reconstruction of a 3-D image of the scattering medium.

* * * * *